US009005942B2

(12) United States Patent
Chen et al.

(10) Patent No.: US 9,005,942 B2
(45) Date of Patent: Apr. 14, 2015

(54) ENHANCED ANIMAL CELL GROWTH USING ULTRASOUND

(75) Inventors: Jie Chen, Edmonton (CA); James Xing, Edmonton (CA); Woon T. Ang, Edmonton (CA); Hilal Gul, Edmonton (CA)

(73) Assignee: Intelligentnano Inc., Edmonton, Alberta (CA)

( * ) Notice: Subject to any disclaimer, the term of this patent is extended or adjusted under 35 U.S.C. 154(b) by 488 days.

(21) Appl. No.: 13/060,851

(22) PCT Filed: Aug. 26, 2009

(86) PCT No.: PCT/CA2009/001188
§ 371 (c)(1),
(2), (4) Date: Jul. 20, 2011

(87) PCT Pub. No.: WO2010/022508
PCT Pub. Date: Mar. 4, 2010

(65) Prior Publication Data
US 2011/0275054 A1 Nov. 10, 2011

Related U.S. Application Data

(60) Provisional application No. 61/091,830, filed on Aug. 26, 2008.

(51) Int. Cl.
*C12N 13/00* (2006.01)
*C12N 5/0789* (2010.01)
*C12M 1/42* (2006.01)

(52) U.S. Cl.
CPC .............. *C12N 5/0647* (2013.01); *C12N 13/00* (2013.01); *C12M 35/04* (2013.01)

(58) Field of Classification Search
None
See application file for complete search history.

(56) References Cited

U.S. PATENT DOCUMENTS

| | | | |
|---|---|---|---|
| 4,530,360 A | 7/1985 | Duarte | |
| 4,879,011 A | 11/1989 | Schram | |
| 5,554,384 A | 9/1996 | Samuels et al. | |
| 6,835,560 B2 | 12/2004 | Greene | |
| 8,079,966 B2 | 12/2011 | El-Bialy et al. | |
| 8,292,834 B2 | 10/2012 | El-Bialy et al. | |
| 2003/0153077 A1* | 8/2003 | Pitt et al. ........................ 435/383 |
| 2004/0191906 A1 | 9/2004 | Holzer | |
| 2004/0197908 A1 | 10/2004 | Ueda et al. | |
| 2006/0106424 A1 | 5/2006 | Bachem | |
| 2007/0020757 A1* | 1/2007 | Zhang et al. ................... 435/354 |
| 2007/0082397 A1* | 4/2007 | Hasson et al. ................. 435/366 |
| 2007/0249046 A1* | 10/2007 | Shields, Jr. ..................... 435/366 |
| 2007/0299539 A1 | 12/2007 | Othman et al. | |
| 2008/0021327 A1 | 1/2008 | El-Bialy et al. | |
| 2010/0034735 A1 | 2/2010 | Chen et al. | |
| 2011/0189748 A1 | 8/2011 | Chen et al. | |
| 2011/0275054 A1 | 11/2011 | Chen et al. | |
| 2012/0059287 A1 | 3/2012 | El-Bialy et al. | |
| 2012/0100525 A1 | 4/2012 | Chen et al. | |
| 2012/0135392 A1 | 5/2012 | El-Bialy et al. | |
| 2013/0022957 A1 | 1/2013 | Chen et al. | |
| 2013/0265856 A1 | 10/2013 | Choi et al. | |

FOREIGN PATENT DOCUMENTS

| | | |
|---|---|---|
| EP | 1566201 | 8/2005 |
| WO | 03/089581 | 10/2003 |
| WO | 03089581 | 10/2003 |
| WO | 2008/004752 | 1/2008 |
| WO | 2008004752 | 1/2008 |
| WO | 2010022508 | 8/2009 |
| WO | 2010/022508 | 3/2010 |
| WO | 2010/022509 | 3/2010 |
| WO | 2013/040688 | 3/2013 |

OTHER PUBLICATIONS

Takagi et al., Journal of Bioscience and Bioengineering, vol. 99, No. 3, pp. 189-196, 2005.*
Parvizi, J. et al., "Low-intensity ultrasound stimulates proteoglycan synthesis in rat chondrocytes by increasing aggrecan gene expression", Journal of Orthopaedic Research, vol. 17, No. 4, pp. 488-494, (1999).
Lin, L. et al., "Ultrasound-induced physiological effects and secondary metabolite (saponin) production in panax ginseng cell cultures", Ultrasound in Med. & Biology, vol. 27, No. 8, pp. 1147-1152, (2001).
Yoon, J.H. et al., "Introducing pulsed low-intensity ultrasound to culturing human umbilical cord-derived mesenchymal stem cells", Biotechnol Letter, vol. 31, pp. 329-335, (2009).
Chisti, Y. "Sonobioreactors: using ultrasound for enhanced microbial productivity", Trends in Biotechnology, vol. 21, No. 2, pp. 89-93, (2003).
Sontag, W. et al., "Expression of heat shock proteins after ultrasound exposure in HL-60 cells", Ultrasound in Med. & Biol., vol. 35, No. 6, pp. 1032-1041, (2009).
Ang, W.T. et al., "Design and implementation of therapeutic ultrasound generating circuit for dental tissue formation and tooth-root healing", IEEE Transactions on Biomedical Circuits and Systems, vol. 4, No. 1, pp. 49-61, (2010).

(Continued)

*Primary Examiner* — Allison Fox
*Assistant Examiner* — Yvonne Pyla
(74) *Attorney, Agent, or Firm* — Evan Law Group LLC

(57) ABSTRACT

A method of increasing the rate of growth of an animal cell or cell culture include the use of ultrasound at a frequency greater than about 1 MHz.

18 Claims, 4 Drawing Sheets

(56) References Cited

OTHER PUBLICATIONS

Figure 1A:

Bradner, J.R. et al., "Qualitative assessment of hydrolytic activities in antarctic microfungi grown at different temperatures on solid media", World Journal of Microbiology & Biotechnology, vol. 15, pp. 131-132, (1999).

Chen, H. et al., "Key technologies for bioethanol production from lignocelluloses", Biotechnology Advances, vol. 28, No. 5, pp. 556-562, (2010).

Doan, N. et al., "In vitro effects of therapeutic ultrasound on cell proliferation, protein synthesis, and cytokine production by human fibroblasts, osteoblasts, and monocytes", J. Oral Maxillofac Surg., vol. 57, pp. 409-419, (1999).

Khanal, S.K. et al., "Ultrasound enhanced glucose release from corn in ethanol plants", Biotechnology and Bioengineering, vol. 98, No. 5, pp. 978-985, (2007).

Kobayashi, Y. et al., "Low-intensity pulsed ultrasound stimulates cell proliferation, proteoglycan synthesis and expression of growth factor-related genes in human nucleus pulposus cell line", European Cells and Materials, vol. 17, pp. 15-22, (2009).

Leung, K-S. et al., "Complex tibial fracture outcomes following treatment with low-intensity pulsed ultrasound", Ultrasound in Med. & Biology, vol. 30, No. 3, pp. 389-395, (2004).

Min, B-H. et al., "Effects of low-intensity ultrasound (LIUS) stimulation on human cartilage explants", Scand J. Rheumatol., vol. 35, pp. 305-311, (2006).

Osawa, K. et al., "Osteoinduction by microbubble-enhanced transcutaneous sonoporation of human bone morphogenetic protein-2", The Journal of Gene Medicine, vol. 11, pp. 633-641, (2009).

Singhania R.R. et al., "Plant-Based biofuels—An introduction", A. "Handbook of Plant-Based Biofuels", CRC Press, pp. 3-12, (2009).

Rubin, C. et al., "The use of low intensity ultrasound to accelerate the healing of fractures", J. Bone Joint Surg. Am., vol. 83, pp. 259-270, (2001).

Soetaert, W. et al., "Biofuels in Perspective", Biofuels, pp. 1-7, John Wiley & Sons LTD, (2009).

Sun, J-S. et al., "In vitro effects of low-intensity ultrasound stimulation on the bone cells", Journal of Biomedical Materials Research, vol. 57, pp. 449-456, (2001).

Nikolic, S. et al., "Ultrasound-assisted production of bioethanol by simultaneous saccharification and fermentation of corn meal", Food Chemistry, vol. 122, pp. 216-222, (2010).

Teather, R.M. et al., "Use of Congo red-polysaccharide interactions in enumeration and characterization of cellulolytic bacteria from the bovine rumen", Applied and Environmental Microbiology, vol. 43, No. 4, pp. 777-780, (1982).

Wood, B.E. et al., "Ultrasound stimulates ethanol production during the simultaneous saccharification and fermentation of mixed waste office paper", Biotechnol Progress, vol. 13, No. 3, pp. 232-237, (1997).

Yang, F. et al., "Enhancement of enzymatic in situ saccharification of cellulose in aqueous-ionic liquid media by ultrasonic intensification", Carbohydrate Polymers, vol. 81, No. 2, pp. 311-316, (2010).

Zhou, S. et al., "Molecular mechanism of low intensity pulsed ultrasound in human skin fibroblast", J. Biol. Chem., vol. 279, pp. 54463-54469, (2004).

Shaheen, M. et al., "Application of low-intensity pulsed ultrasound to increase bio-ethanol production", Renewable Energy, vol. 57, pp. 462-468, (2013).

Zhao, Y. et al., "Applications of ultrasound to enhance mycophenolic acid production" Ultrasound in Medicine & Biology, vol. 38, issue 9, pp. 1582-1588, (2012).

Radel, S. et al., "Viability of yeast cells in well controlled propagating and standing ultrasonic plane waves", Ultrasonics, vol. 38, pp. 633-637, (2000).

Sainz Herran, N. et al., "Influence of ultrasound amplitude and duty cycle on fungal morphology and broth rheology of *Aspergillus terreus*", World J. Microbiol Biotechnol, vol. 26, pp. 1409-1418, (2010).

Saif Ur Rehman, M. et al., "Use of ultrasound in the production of bioethanol from lignocellulosic biomass", Energy Education Science and Technology Part A: Energy Science and Research, vol. 30, issue 2, pp. 1391-1410, (2013).

Ohgren, K., et al., "High temperature enzymatic prehydrolysis prior to simultaneous saccharification and fermentation of steam pretreated corn stover for ethanol production", Enzyme and Microbial Technology, vol. 40, pp. 607-613, (2007).

Gamauf. C. et al., "Characterization of the bga1-encoded glycoside hydrolase family 35 β-galactosidase of hypocrea jecorina with glacto-β-D-galactanase activity", The FEBS Journal, vol. 274, pp. 1691-1700, (2007).

Xu, P. et al., "Low-intensity pulsed ultrasound-mediated stimulation of hematopoietic stem/progenitor cell viability, proliferation and differentiation in vitro", Biotechnology Letters, vol. 34, issue 10, pp. 1965-1973, (2012).

International Search Report dated Dec. 9, 2009 for PCT application No. PCT/CA2009/001189, 11 pages.

Xie, C.-g. et al., "Marrow mesenchymal stem cells transduced with TPO/FL genes as support for ex vivo expansion of hematopoietic stem/progenitor cells", Cellular and Molecular Life Sciences, vol. 62, pp. 2495-2507, (2005).

Xing, J.Z. et al., "Ultrasound-enhanced monoclonal antibody production", Ultrasound in Medicine and Biology, vol. 38, No. 11, pp. 1949-1957, (2012).

Wofsy, D. et al., "Successful treatment of autoimmunity in NZB/NZW $F_1$ mice with monoclonal antibody to L3T4", Journal of Experimental Medicine, vol. 161, pp. 378-391, (1985).

Yi, H. et al., "Depleting anti-CD4 monoclonal antibody (GK1.5) treatment: influence on regulatory CD4+CD25+Foxp3+ T cells in mice", Transplantation, vol. 85, No. 8, pp. 1167-1174, (2008).

Markvicheva, E. et al., "The effect of low-intensity ultrasound on hybridoma cell proliferation and monoclonal antibody production in hollow fiber bioreactor", European Journal of Cell Biology, vol. 69, No. suppl. 42, #465, p. 155, Conference Abstract from the $21^{st}$ Annual Meeting of the German Society for Cell Biology, Hamburg, Germany, Mar. 24-28, 1996.

Lv, Y. et al., "Effects of low-intensity pulsed ultrasound on cell viability, proliferation and neural differentiation of induced pluripotent stem cells-derived neural crest stem cells", Biotechnology Letters, vol. 35, issue 12, pp. 2201-2212, (2013).

International Search Report dated Dec. 10, 2009, for PCT application No. PCT/CA2009/001188, 11 pages.

Bensinger, W. et al., "Improving stem cell mobilization strategies: future directions", Bone Marrow Transplantation, vol. 43, pp. 181-195, (2009).

Birch, J.R. et al., "Antibody production", Advanced Drug Delivery Reviews, vol. 58, pp. 671-685, (2006).

Bordignon, C. "Stem-cell therapies for blood diseases", Nature, vol. 441, pp. 1100-1102, (2006).

Brada, S. et al., "The supportive effects of erythropoietin and mast cell growth factor on CD34+/CD36− sorted bone marrow cells of myelodysplasia patients", Blood, vol. 88, pp. 505-510, (1996).

Brada, S.J.L. et al., "Characterization of the erythropoiesis in myelodysplasia by means of ferrokinetic studies, in vitro erythroid colony formation and soluble transferrin receptor", Leukemia, vol. 12, pp. 340-345, (1998).

Bradley, M.B. et al., "Cord blood immunology and stem cell transplantation", Human Immunology, vol. 66, pp. 431-446, (2005).

Brugger, W. et al., "Reconstitution of hematopoiesis after high-dose chemotherapy by autologous progenitor cells generated ex vivo", The New England Journal of Medicine, vol. 333, No. 5, pp. 283-287, (1995).

Choi, W.H. et al., "Low-intensity ultrasound increased colony forming unit-fibroblasts of mesenchymal stem cells during primary culture", Tissue Engineering: Part C, vol. 17, No. 5, pp. 517-526, (2011).

Conneally, E. et al., "Expansion in vitro of transplantable human cord blood stem cells demonstrated using a quantitative assay of their lympho-myeloid repopulating activity in nonobese diabetic-scid/scid mice", Proceedings of the National Academy of Sciences of the United States of America, vol. 94, pp. 9836-9841, (1997).

(56) References Cited

OTHER PUBLICATIONS

Copelan, E.A. "Hematopoietic stem-cell transplantation", The New England Journal of Medicine, vol. 354, No. 17, pp. 1813-1826, (2006).
Dahlberg, A. et al., "Ex vivo expansion of human hematopoietic stem and progenitor cells", Blood, vol. 117, No. 23, pp. 6083-6090, (2011).
El-Bialy, T. "Therapeutic ultrasound applications in craniofacial growth, healing and tissue engineering", Rejuvenation Research, vol. 10, No. 3, pp. 367-371, (2007).
Gluckman, E. "Ten years of cord blood transplantation: from bench to bedside", British Journal of Haematology, vol. 147, pp. 192-199, (2009).
Guilak, F. et al., "Control of stem cell fate by physical interactions with the extracellular matrix", Cell Stem Cell, vol. 5, pp. 17-26, (2009).
Gul, H. et al., "Valproic acid increases CXCR4 expression in hematopoietic stem/progenitor cells by chromatin remodeling", Stem Cells and Development, vol. 18, No. 6, pp. 831-838, (2009).
Gul, H. et al., "Magnetic carbon nanotube labelling for haematopoietic stem/progenitor cell tracking", Nanotechnology, vol. 21, pp. 1-9, (2010).
Harris, G.R., "Progress in medical ultrasound expositmetry", IEEE Transactions on Ultrasonics, Ferroelectrics, and Frequency Control, vol. 52, No. 5, pp. 717-736, (2005).
Heckman, J.D. et al., "Acceleration of tibial fracture-healing by non-invasive, low-intensity pulsed ultrasound", The Journal of Bone & Joint Surgery, vol. 76-A, No. 1, pp. 26-34, (1994).
Iwashina, T. et al., "Low-intensity pulsed ultrasound stimulates cell proliferation and proteoglycan production in rabbit intervertebral disc cells cultured in alginate", Biomaterials, vol. 27, pp. 354-361, (2006).
Kaufmann, H. et al., "Metabolic engineering of mammalian cells for higher protein yield", Gene Transfer and Expression in Mammalian Cells, Chapter 15, pp. 457-469, (2003).
Kaushansky, K. "Thrombopoietin and the hematopoietic stem cell", Blood, vol. 92, No. 1, pp. 1-3, (1998).
McNiece, I. et al., "Ex vivo expanded peripheral blood progenitor cells provide rapid neutrophil recovery after high-dose chemotherapy in patients with breast cancer", Blood, vol. 96, No. 9, pp. 3001-3007, (2000).
Mottram, P.L. et al., "Transgenic anti-CD4 monoclonal antibody secretion by mouse segmental pancreas allografts promotes long term survival", Transplant Immunology, vol. 8, pp. 203-209, (2000).
Petzer, A.L. et al., "Differential cytokine effects on primitive (CD34+ CD38−) human hematopoietic cells: novel responses to Flt3-ligand and thrombopoietin", The Journal of Experimental Medicine, vol. 183, pp. 2551-2558, (1996).
Praloran, V. et al.,"Blood erythroid progenitors (CFU-E and BFU-E) in acute lymphoblastic leukemias", Blut, vol. 58, pp. 75-78, (1989).
Qiu, Y. et al., "The correlation between acoustic cavitation and sonoporation involved in ultrasound-mediated DNA transfection with polyethylenimine (PEI) in vitro", Journal of Controlled Release, vol. 145, pp. 40-48, (2010).
Rodrigues, M.E. et al., "Technological progresses in monoclonal antibody production systems", Biotechnology Progress, vol. 26, No. 2, pp. 332.351, (2010).
Rubinstein, P. "Why cord blood?", Human Immunology, vol. 67, pp. 398-404, (2006).
Scheven, B.A.A. et al., "Therapeutic ultrasound for dental tissue repair", Medical Hypotheses, vol. 73, pp. 591-593, (2009).
Shah, A.J. et al., "Flt3 ligand induces proliferation of quiescent human bone marrow $CD34^+CD38^-$ cells and maintains progenitor cells in vitro", Blood, vol. 87, No. 9, pp. 3563-3570, (1996).
Sriram, S. et al., "In vivo immunomodulation by monoclonal anti-CD4 antibody II. Effect on T cell response to myelin basic protein and experimental allergic encephalomyelitis", The Journal of Immunology, vol. 141, No. 2, pp. 464-468, (1988).
Doherty, T.A. et al., "CD4+ cells are required for chronic eosinophilic lung inflammation but not airway remodeling", American Journal of Physiology—Lung Cellular and Molecular Physiology, vol. 296, pp. L229-L235, (2009).
Villaron, E.M. et al., "In leukapheresis products from non-Hodgkin's lymphoma patients, the immature hematopoietic progenitors show higher CD90 and CD34 antigenic expression", Transfusion and Apheresis Science, vol. 37, pp. 145-156, (2007).
Wurm, F.M. "Production of recombinant protein therapeutics in cultivated mammalian cells", Nature Biotechnology, vol. 22, No. 11, pp. 1393-1398, (2004).
Zhang, Z-J. et al., "The effects of pulsed low-intensity ultrasound on chondrocyte viability, proliferation, gene expression and matrix production", Ultrasound in Medicine & Biology, vol. 29, No. 11, pp. 1645-1651, (2003).
Ziskin, M.C., "Applications of ultrasound in medicine—comparison with other modalities", Ultrasound: Medical Applications, Biological Effects, and Hazard Potential, pp. 49-59, (1987).
International Search Report and Written Opinion dated Jan. 11, 2013 for PCT application No. PCT/CA2012/000873, 14 pages.
Regueira, T.B. et al., "Molecular basis for mycophenolic acid biosynthesis in *Penicillium brevicompactum*", Applied and Environmental Microbiology, vol. 77, No. 9, pp. 3035-3043, (2011).
Gul-Uludag, H. et al., "Abstract of Ultrasound stimulation enhances proliferation of hematopoietic stem/progenitor cells: Implications for clinical transplantation, gene and cellular therapies", Annual Conference of International Society for Cellular Therapy, Philadelphia, PA, May 25, Cytotherapy 12:40, (2010).
Barnett, S.B. et al., "Is pulsed ultrasound mutagenic?", Ultrasound Med. Biol., Supplemental 2, pp. 45-48, (1983).
Pui, P.W.S. et al., "Batch and semicontinuous aggregation and sedimentation of hybridoma cells by acoustic resonance fields", Biotechnology Prog., vol. 11, No. 2, pp. 146-152, (1995).
Yoon, J.H. et al.; Introducing Pulsed Low-Intensity Ultrasound to Culturing Human Umbilical Cord-Derived Mesenchymal Stem Cells; Biotechnol.; Lett.; 2009; vol. 31; pp. 329-335.
Parvizi, Javad et al.; Low Intensity Ultrasound Stimulates Proteoglycan Synthesis in Rat Chondrocytes by Increasing Aggrecan Gene Expression; Journal of Orthopaedic Research; 1999; vol. 17, No. 4; pp. 488-494.
Lin, Lidong et al.; Ultrasound-Induced Physiological Effects and Secondary Metabolite (Saponin) Production in Panax Ginseng Cell Cultures; Ultrasound in Med. & Viol.; vol. 27, No. 8; pp. 1147-1152, 2001.
El-Bialy, T. et al., "Cell expansion genes expression by therapeutic ultrasound. Pros and cons", Canadian Accoustics, vol. 36, No. 3, pp. 40-41, (2008).

\* cited by examiner

ENHANCED ANIMAL CELL GROWTH USING ULTRASOUND

CROSS REFERENCE TO RELATED APPLICATIONS

This application claims the priority benefit of U.S. Provisional Application No. 61/091,830 filed on Aug. 26, 2008 entitled "METHOD TO INCREASE THE RATE OF PROTEIN EXPRESSION IN CELL", the contents of which are incorporated herein by reference.

FIELD OF THE INVENTION

The present method relates to methods of increasing animal cell growth in cell culture by exposing the culture to ultrasonic stimulation.

BACKGROUND OF THE INVENTION

It is commonplace to grow animal cells in cell culture. Mass culture of animal cell lines is fundamental to the manufacture of viral vaccines and many products of biotechnology. Biological products produced by recombinant DNA (rDNA) technology in animal cell cultures include enzymes, synthetic hormones, immunobiologicals (monoclonal antibodies, interleukins, lymphokines), and anticancer agents. Although many simpler proteins can be produced using rDNA in bacterial cultures, more complex proteins that are glycosylated (carbohydrate-modified) currently must be made in animal cells.

Many different cell types may be grown in cell culture, and are of great interest to researchers in many different fields. Such cells include stem cells. Stem cells differ from other kinds of cells in the body. All stem cells—regardless of their source—have three general properties: they are capable of dividing and renewing themselves for long periods; they are unspecialized; and they can give rise to specialized cell types.

The specific factors and conditions that allow stem cells to remain unspecialized are of great interest to scientists. It has taken scientists many years of trial and error to learn to derive and maintain stem cells in the laboratory without them spontaneously differentiating into specific cell types. Therefore, understanding the signals in a mature organism that cause a stem cell population to proliferate and remain unspecialized until the cells are needed. Such information is critical for scientists to be able to grow large numbers of unspecialized stem cells in the laboratory for further experimentation.

Stem cells are unspecialized. One of the fundamental properties of a stem cell is that it does not have any tissue-specific structures that allow it to perform specialized functions. For example, a stem cell cannot work with its neighbors to pump blood through the body (like a heart muscle cell), and it cannot carry oxygen molecules through the bloodstream (like a red blood cell). However, unspecialized stem cells can give rise to specialized cells, including heart muscle cells, blood cells, or nerve cells.

Scientists are attempting to find new ways to control stem cell differentiation in the laboratory, thereby growing cells or tissues that can be used for specific purposes such as cell-based therapies or drug screening.

Adult stem cells typically generate the cell types of the tissue in which they reside. For example, a blood-forming adult stem cell in the bone marrow normally gives rise to the many types of blood cells. It is generally accepted that a blood-forming cell in the bone marrow—which is called a hematopoietic stem cell—cannot give rise to the cells of a very different tissue, such as nerve cells in the brain. Experiments over the last several years have purported to show that stem cells from one tissue may give rise to cell types of a completely different tissue.

There are many ways in which human stem cells can be used in research and the clinic. Studies of human embryonic stem cells will yield information about the complex events that occur during human development. A primary goal of this work is to identify how undifferentiated stem cells become the differentiated cells that form the tissues and organs. Scientists know that turning genes on and off is central to this process. Some of the most serious medical conditions, such as cancer and birth defects, are due to abnormal cell division and differentiation. A more complete understanding of the genetic and molecular controls of these processes may yield information about how such diseases arise and suggest new strategies for therapy. Predictably controlling cell proliferation and differentiation requires additional basic research on the molecular and genetic signals that regulate cell division and specialization. While recent developments with iPS cells suggest some of the specific factors that may be involved, techniques must be devised to introduce these factors safely into the cells and control the processes that are induced by these factors.

Human stem cells could also be used to test new drugs. For example, new medications could be tested for safety on differentiated cells generated from human pluripotent cell lines. Other kinds of cell lines are already used in this way. Cancer cell lines, for example, are used to screen potential anti-tumor drugs. The availability of pluripotent stem cells would allow drug testing in a wider range of cell types. However, to screen drugs effectively, the conditions must be identical when comparing different drugs. Therefore, scientists will have to be able to precisely control the differentiation of stem cells into the specific cell type on which drugs will be tested. Current knowledge of the signals controlling differentiation falls short of being able to mimic these conditions precisely to generate pure populations of differentiated cells for each drug being tested.

Perhaps the most important potential application of human stem cells is the generation of cells and tissues that could be used for cell-based therapies. Today, donated organs and tissues are often used to replace ailing or destroyed tissue, but the need for transplantable tissues and organs far outweighs the available supply. Stem cells, directed to differentiate into specific cell types, offer the possibility of a renewable source of replacement cells and tissues to treat diseases including Alzheimer's diseases, spinal cord injury, stroke, burns, heart disease, diabetes, osteoarthritis, and rheumatoid arthritis.

There is a need in the art for methods to enhance proliferation of stem cells in cell culture, to permit more rapid and efficient study of stem cells and their potential uses.

Ultrasonic stimulation creates "microcavitation" or the creation of minute bubbles in a liquid known as "microcavities." With each sound wave, these bubbles expand and contract, creating tremendous force and turbulence on a microscopic scale. In some cases, this sound wave is powerful enough to collapse the cavities, which causes even more extreme turbulence, high temperatures, and free radicals in the vicinity of the former cavity. These collapses are powerful enough to dislodge or even destroy cells.

Ultrasonic applications rely on these processes—one common use of ultrasound is as an effective cleaning agent; if the intensity is high enough, collapse cavitation is the dominant factor in the cells' environment. This can strip harmful bacteria off of a surface, and even kill a large number of them. The effectiveness of this technique has been proven by applying ultrasound to one end of a glass tube, using frequencies around 100 kHz and intensities around 40 W/cm$^2$—it was found that approximately 88% of the bacteria were removed from the surface of the tube. Similar experiments have been carried out in a variety of situations, including stripping biofilms off of reverse osmosis membranes. Ultrasound is now actively sold to laboratories as a cleaning aid.

As well as dislodging bacteria, very high intensity ultrasound (>10 W/cm$^2$) has been used to kill suspended bacteria—this relies on collapse cavitation to rend the bacteria's membrane.

Applications also exist for lower-intensity ultrasound; it has long been held that ultrasonic waves can improve the rate of bone growth and indeed, almost 80% of North American physiotherapists possess ultrasonic emitters for the purpose of encouraging speedy recovery. A recent study has indicated that only low-intensity ultrasound is effective in this situation, and low-intensity pulsed ultrasound (LIPUS) devices are currently being marketed for this purpose. One method has been revealed in U.S. Pat. No. 4,530,360 to Duarte (1982).

A method of using low-intensity pulsed ultrasound to aid the healing of flesh wounds is shown in U.S. Pat. Application 2006/0106424 A1 by Bachem (2005). The method utilizes ultrasound to increase the phagocytotic action of the human body's macrophages, and relies on similar theoretical principles to accomplish its aims. However, the method provides no solution for the use of ultrasound outside the confines of a wound.

U.S. Patent Application No. US 2003/0153077 A1 details a method in which low-intensity ultrasound can stimulate the growth of biofilms and other cells—by balancing the beneficial turbulence produced by collapse cavitation with its accompanying negative effects, it was found that low-intensity ultrasound can improve growth rates of cells by up to 50%. The experimenters tested their findings on human and bacterial cells, using frequencies from about 20 kHz to about 1 MHz and intensities encompassing the range from 1 to 5000 mW/cm$^2$. Unfortunately, though increased cell growth is beneficial to the fermentation process, the parameters investigated by this group do not provide the optimal rate of protein expression in fermentation processes.

SUMMARY OF THE INVENTION

The present invention provides a method of increasing the rate of cell proliferation in animal cells grown in cell culture, by stimulating them with calibrated ultrasound.

In one aspect, the invention comprises a method of enhancing the rate of cell growth in an animal cell culture through exposure to ultrasound of specified frequencies and intensities. These methods are beneficial to cells in the vast majority of environments, creating turbulence on the microscopic scale in the area immediately adjacent to the walls of the cells and other solid surfaces.

The ultrasound may have a frequency between about 1 MHz and about 2 MHz, depending inter alia on the species and type of cell used in culture. In one embodiment, the ultrasound has a frequency between about 1.4 MHz to about 1.6 MHz. In one embodiment, it consists of a pulsed ultrasound, which assists in minimizing temperature increase of the environment. In one embodiment, pulses generated at a duty cycle of approximately 4:1 (off:on), with a pulse period of approximately 1 second, are effective. In one embodiment, the ultrasound is calibrated to achieve a balance of the harmful effects of "collapse cavitations" caused by the ultrasound and the beneficial turbulence it affords the cells, allowing increased nutrient uptake and metabolic byproduct expulsion.

In one aspect of the invention, there is also a method of sensing the intensity of the ultrasonic waves employed, as "felt" by the target cells. This is not, however, necessary in all circumstances, and the method can proceed without such detection. The intensity measurement can be taken with any commercial ultrasound-measuring device. In one embodiment, the method further comprises the step of relaying collected information back to the ultrasonic emitter if said sensor is employed. This may be through a wired or wireless connection.

In another aspect, the invention comprises a method of correcting the emitted output to maximize the effectiveness of the ultrasound, based on the sensed intensities, if said sensor is employed. This assists in maximizing cell growth rates.

The ultrasound may possess an intensity greater than about 10 mW/cm$^2$ up to about 5000 mW/cm$^2$, depending on the fragility of the cells in culture.

In one embodiment, the ultrasound can be directed such that reflections and interference are minimized, or tuned to give maximum effectiveness to the ultrasonic emission.

BRIEF DESCRIPTIONS OF THE DRAWINGS

Figure 1B:
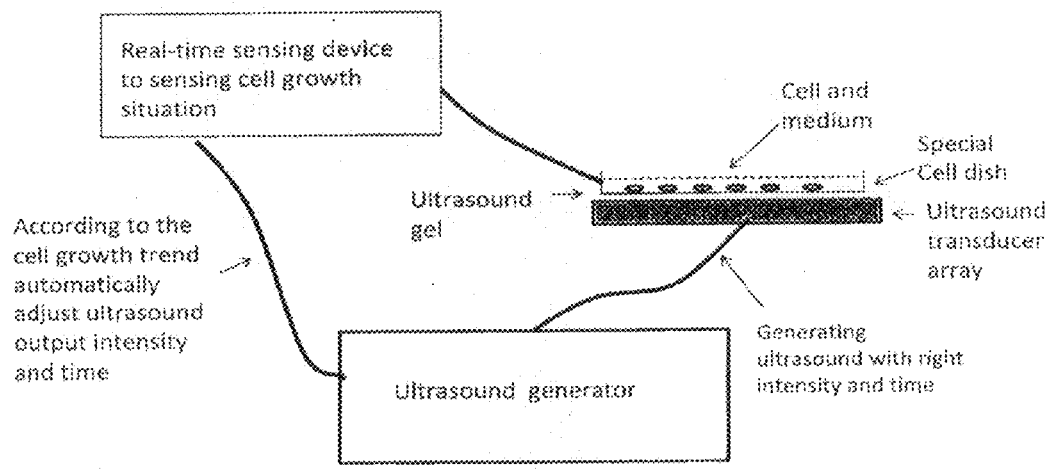

In order that the above-recited and other features and advantages of the present invention will be readily understood, a more particular description of the invention is given. A specific example thereof is detailed, the result of which are illustrated in the appended figures. The following example is only a single embodiment of the invention, and is not to be considered in any way the limit of its scope. In the accompanying figures:

FIG. 1A is a depiction of one embodiment of the invention described herein, allowing enhanced proliferation of stem cells in culture. FIG. 1B is a schematic representation of an ultrasound system employing system feedback.

Figure 2:
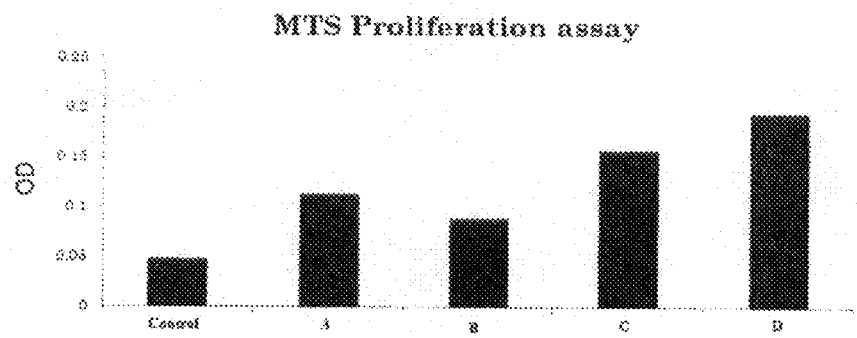

FIG. 2 shows a graph comparing proliferation of LP-HSPC after ultrasound treatment. Control: no ultrasound. A: 40 mW/cm$^2$ B: 70 mW/cm$^2$, C: 60 mW/cm$^2$, D; 50 mW/cm$^2$. The vertical index is OD (optical density). In these tests, a cytokine cocktail of growth factors (SCF: 100 ug/ml, TPO:50 ug/ml, Flt3-ligand: 50 ug/ml), were used.

Figure 3A:
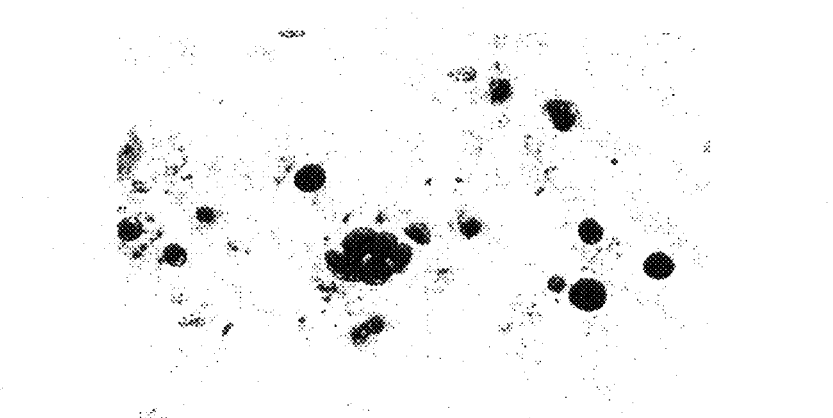
Figure 3B:

FIG. 3A shows a micrograph of CD34+ Stem cells morphology at day 0 and FIG. 3B shows cell morphology at day 5 after 4 days of ultrasound stimulation.

Figure 4:
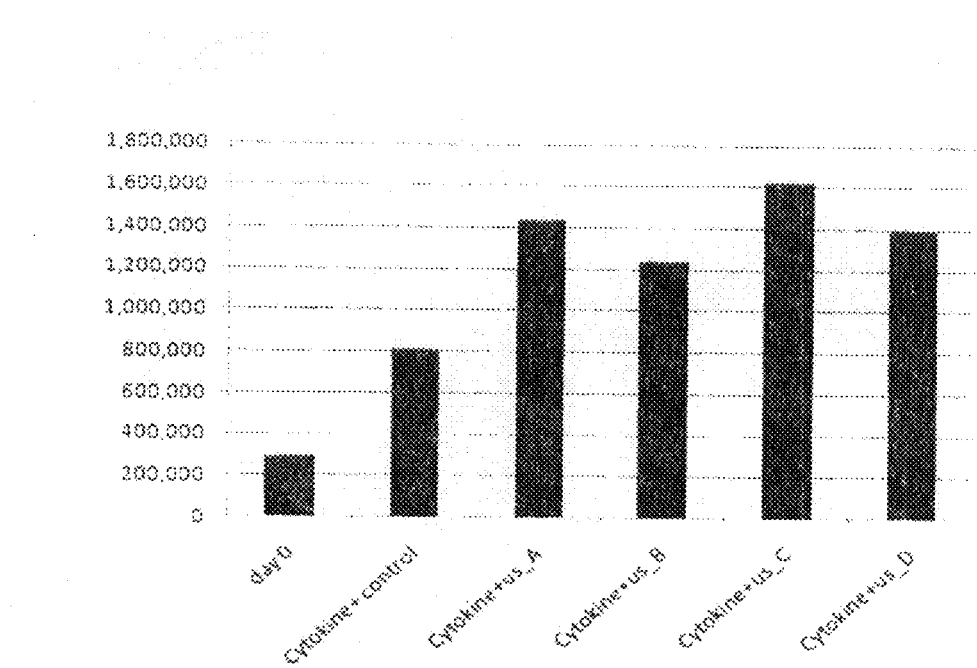

FIG. 4 shows a comparison of cell numbers of HSPC grown with ultrasound treatment of different intensities.

Figure 5:
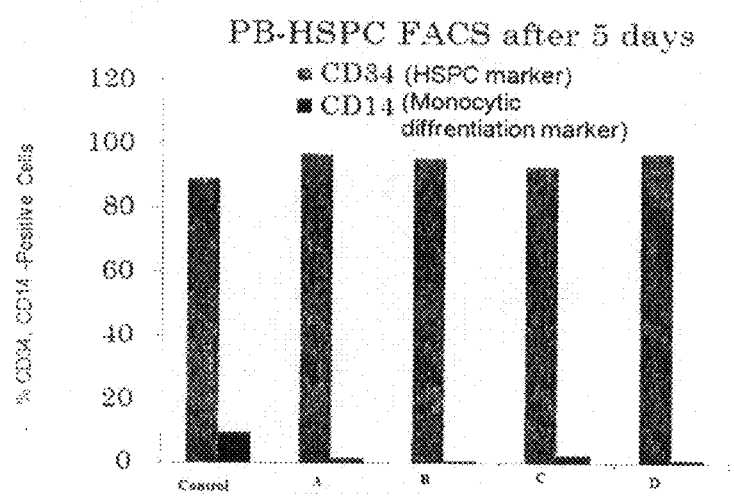

FIG. 5 shows a graph demonstrating that ultrasound treated HSPC (human hematopoietic stem/progenitor cells) do not differentiate. Here the intensities are different, A: 40 mW/cm$^2$, B: 70 mW/cm$^2$, C: 60 mW/cm$^2$, D: 40 mW/cm$^2$. The assay is flowcytometry (FACS), which detects quantitatively expression of cell surface markers for CD34 and CD14.

DETAILED DESCRIPTION OF THE EMBODIMENTS

The presently presented methods of the invention will be better understood by referring to the following examples with their attached figures. The methods of the present invention, as generally described herein, can be practiced and varied in many ways. Thus, the following more detailed description of the methods of the present invention is not intended to limit the scope of the invention, as claimed. Instead, the detailed description is merely representative of the presently considered embodiments.

As used herein, the term "cell culture" may include any group of cells grown in a controlled environment. The targeted animal cells may be any cell or cell line of animal origin, including without limitation, primary cells, immortalized cells, or stem cells. The cell culture may be in suspension, a two-dimensional or three-dimensional adherent culture, or any other cell culture system.

The term "animal" is used to refer to the major group of multi-cellular, eukaryotic organisms of the kingdom Animalia or Metazoa, which of course includes mammals and insects.

The term "stem cell" is a cell which possesses the property of self-renewal and also the property of potency. Self-renewal refers to the ability to undergo at least one generation of mitotic cell division while maintaining potency. Potency means the cell is undifferentiated and has the ability to mature into one or more different cell types. Stem cells may be totipotent, pluripotent, multipotent, oligopotent or unipotent. Stem cells may be fetal, embryonic or adult in origin.

The term "about" is used to denote an acceptable range higher or lower than the stated figure, and no greater than 10% higher or lower in any event. It may also allow for a level of uncertainty or imprecision in devices or instruments used to measure the stated figure.

The present invention may be applied to animal cells or cell culture of a wide range of origin or cell type. In one embodiment, the cell or cell culture comprises stem cells, T-cells or islet cells. The enhanced cell growth may be used in any application, where the cells themselves are useful, or the cells are used to produce useful biomolecules or compounds.

It is not known with certainty why ultrasound applied in accordance with the present invention enhances stem cell proliferation. Without being limited to any one theory, it appears that implementation of the present invention increases protein expression by allowing more rapid transport of essential materials into the cell, and allowing quicker dispersion of metabolic by-products away from the cell.

Though most cell culture techniques address this problem by stirring or shaking the cell cultures, we believe that a microscopic buffer remains around solid surfaces or cell walls in which fluid movement is greatly constrained. If the fluid immersing the cell is stagnant in the area directly adjacent to the cell, it is not conducive to the transport of small molecules—oxygen, amino acids, carbon dioxide, etc.—away from or towards the cell.

A liquid surrounding a cell culture contains bubbles of gas which compress and relax, causing them to contract and expand, when exposed to ultrasound. This movement creates resultant forces on the liquid surrounding the gas bubbles—when the bubble is compressed, liquid is "pulled" into the area around the now-smaller bubble, and when the bubble expands, liquid is pushed away. This causes considerable turbulence on the microscopic level. This turbulence is even slightly topical, as gas bubbles will preferentially form near cell walls or solid surfaces, precisely the original locations of the stagnancy.

If the pressures are high enough (this is caused by ultrasound of a high intensity), bubbles can collapse down to nothing. Simple thermodynamics will demonstrate that the temperature will rise precipitously in such an incidence—one study claims temperatures as high as 5000 K—and the collapse results in a shock wave of heat and "shear force," or force directed towards the bubble's center. The collapse produces turbulence on a massive scale, allowing even faster transfer of nutrients and wastes—but at the same time, the heat and force may be intense enough to tear open the cell wall itself. The intensity and frequency of ultrasound of the present invention affords a balance between the harmful and beneficial effects of the cavitations.

We have found that ultrasound has beneficial effects on animal cell growth in cell culture when applied at a high frequency, greater than about 1 MHz. Prior art use of ultrasound stimulation involved frequencies in the range of 20 kHz to 1 MHz. We have surprisingly found that that the optimal frequency in many cases was higher than 1 MHz. Thus, in one embodiment, the ultrasound frequency is greater than about 1 MHz, and less than about 2 MHz. Around 1.5 MHz, tests revealed that many cell types, including stem cells and other animal cells, were allowed maximum "micro-agitation" while only sustaining minimal damages to cellular structure. Therefore, in one embodiment, the ultrasound is greater than about 1.4 MHz, and less than about 1.6 MHz.

This high frequency range is surprising as there is no theoretical basis to predict increased effectiveness, because higher frequencies are conventionally associated with decreased effectiveness. So far, no prior art has suggested the use of such a frequency range to stimulate the growth or protein expression of cells.

The intensity of the ultrasound energy may be greater than about 5 mW/cm$^2$ up to about 5000 mW/cm$^2$. In one embodiment, the intensity is preferably between about 40 mW/cm$^2$ and about 80 mW/cm$^2$, and in one embodiment, an optimal intensity was about 60 mW/cm$^2$.

In one embodiment, the invention comprises the use of ultrasound to increase the proliferation of stem cells. In recent years, stem cells have garnered much attention for their unique ability to differentiate into a host of different tissue types found in the human body. The ability of ultrasound to increase protein expression increases the proliferation of stem cells in cell culture.

Different cells have different strengths and weaknesses, and all cells may not require the same frequencies and intensities. Cells from different species or sources may be significantly different in this regard. The method herein provides the windows of frequencies and intensities that allow for optimal performance among these difference varieties of cells.

In one embodiment, the cells in question are subjected to ultrasonic stimulation from an ultrasonic emitter placed near enough to the target area to deliver waves of a specific frequency and intensity. Ultrasound is applied by a piezoelectric transducer to a cell culture in an enclosed conventional flask or disk. The transducer may be positioned to ensure maximum and uniform distribution of the ultrasound throughout the growth medium. In one embodiment, the ultrasound transducer is placed in physical contact with the vessel, using standard ultrasound gel, as shown in FIG. 1.

In one embodiment, the ultrasound is applied during logarithmic growth phase of a cell culture; however, its beneficial effects may be realized during any growth phase.

Sustained stimulation with ultrasound is not necessary, increased growth rate or protein expression may be obtained by applying ultrasound in intervals less than one hour per 24 hour period. In one embodiment, stimulation intervals of only between about 10 minutes and about 20 minutes per 24 hour period is all that is required to reap benefits of LIPUS.

Optimization of a suitable frequency and intensity may be determined by empirical study, without undue experimentation by those skilled in the art. In general, however, prokaryotic cells are naturally more durable than eukaryotic cells and thus can withstand a higher intensity ultrasonic stimulation. Intensity ranges have been briefly discussed in the patent application of Pitt et al, entitled "METHOD TO INCREASE THE RATE OF CELL GROWTH" (Pub. No. US 2003/0153077 A1), the contents of which are incorporated by reference, where permitted. The conclusions reached therein place the approximate intensity ranges for eukaryotic cells at 8-50 mW/cm² and for prokaryotic cells at 2-2.2 W/cm². All trials conducted in the Pitt et al. patent use a frequency of 70 kHz.

In one embodiment, the application of ultrasound energy is pulsed, as prolonged exposure can cause heat buildup and damage the treated cells. The duration and timing of the pulses may again be chosen by one skilled in the art by empirical study. In one embodiment, a duty cycle of 1:4 and a 1 s cycle was utilized in our trials (that is, 200 µs of activity followed by 800 µs of 'silence') The on/off ratio and cycle duration may be varied as required or desired. Other duty cycles may be suitable, depending inter alia on the species of cell, the frequency and intensity of the ultrasound.

When several features of the present invention are combined, the resulting application may be termed "LIPUS", which refers to low-intensity pulsed ultrasound.

In one embodiment, the invention comprises the use of an ultrasound sensor, operatively connected to the ultrasound transmitter, permitting a feedback loop control over frequency and intensity. The intensity measurement can be taken with any suitable ultrasound-measuring device, which are commercially available. In one embodiment, the method further comprises the step of relaying collected information back to the ultrasonic emitter if said sensor is employed. This may be through a wired or wireless connection. A schematic representation of such a setup employing a feedback sensor is shown in FIG. 1B. The feedback loop is used to maintain the ultrasound frequency and intensity at a pre-determined level or range.

As mentioned above, these methods are suitable for use with cells grown in controlled environments, including those in suspension.

The present invention may be embodied in other specific forms without departing from its structures, methods, or other essential characteristics as broadly described herein and claimed hereafter. The described embodiments are to be considered in all respects only as is, therefore, indicated by the appended claims, rather than by the foregoing description. All changes that come within the meaning and equivalence of the claims are to be embraced within their scope.

EXAMPLES

The following examples are intended to be illustrative of the claimed invention, but not be limiting in any manner.

Example 1

Isolation of CD34+ Hematopoietic Stem/Progenitor Cells (HSPC)

Leukophoresis product (LP) was obtained with the patients' informed consent (in accordance with the institutional guidelines approved by the Human Research Ethics Board of the University of Alberta).

LP was used to isolate CD34+ hematopietic stem/progenitor cells (HSPC) using immunomagnetic beads (Miltenyi-Biotec, Auburn, Calif.) according to the manufacturer's instructions. Briefly, light-density mononuclear cells were separated by density gradient centrifugation over 60 percent Percoll (GE Healthcare, Quebec, Canada), labeled with a CD34+ antibody (QBEND 10) and passed through a positive selection column. The purity of isolated CB CD34+ cells was more than 92% as determined by fluorescence-activated cell sorter (FACS) analysis.

Example 2

Stimulation with Low-Intensity Pulsed Ultrasound (LIPUS)

All cells were then maintained in Iscove's modified Dulbecco's medium (IMDM, GibcoBRL, Long Island, N.Y., USA) supplemented with 20% bovine growth serum (BGS; Hyclone, Logan, Utah, USA) and combination of cytokines (SCF: 100 ug/ml, TPO: 50 ug/ml, Flt3-ligand: 50 ug/ml) for four days as described below.

To stimulate the cultured cells with low-intensity pulsed ultrasound (LIPUS), a device producing a 1.5-MHz ultrasound wave, 20% duty cycle, with adjustable output intensity between 30 mW/cm² to 100 mW/cm² was used To enable cultured cells to be treated by ultrasound, four ultrasound transducers were fitted on a plastic frame and connected to the control panel of the signal generator via four independent cables. The cells ($3 \times 10^5$) were seeded in 12-well plates for all the experiments. The operation of the transducers was checked before each experiment. The plates were placed on ultrasound transducers using a coupling gel and different intensities (40 mW/cm², 50 mW/cm², 60 mW/cm², 70 mW/cm²) were applied to the plates for 10 min per 24 hours, for four days. The untreated plates were always put in a separate incubator for control purposes.

Example 3

Cell Proliferation and Viability

Cell proliferation and viability was assessed at day 5 by trypan blue exclusion and 3-(4,5-dimethylthiazol-2-yl)-5-(3carboxymethoxyphenyl)-2-(4-sulfophenyl)-2H-tetrazolium (MTS) cytotoxicity assay, using CellTiter 96 AQueous One Solution (Promega, Madison, Wis.). Briefly, $3 \times 10^5$ cells per well were stimulated by LIPUS in combination with a cytokine cocktail (SCF: 100 ug/ml, TPO:50 ug/ml, Flt3-ligand: 50 ug/ml) for four days. For trypan blue exclusion assay, cells were resuspended in culture medium were stained by addition an equal volume of 0.4% trypan blue (Sigma, St. Louis, Mo.) in PBS and counted using a Neubauer haemocytometer.

In order to perform MTS assay, CellTiter 96 AQueous One Solution (20 µl per 100 µl medium) was added into each well, and cells were incubated at 37° C. for 1-4 h. The absorbance (490 nm) was measured, and cell proliferation ratios were calculated as the ratio of absorbance in treated cells versus that in untreated cells.

Compared to HSPC without LIPUS stimulation, the number of HSPC with ultrasound stimulation increased by about 400% after four days of culture (FIG. 2).

Example 4

Morphological Evaluation of the Cells

LIPUS-expanded cells were spun for cytospin preparation. Cytospin preparations were stained with May-Grünwald-Giemsa. Cytospots were washed with distilled water and allowed to air-dry before analysis under a microscope.

The morphology of the control and ultrasound-stimulated HSPCare presented in FIGS. 3A and 3B respectively.

Example 5

FACS Analysis

The surface expression of CD34 (hematopoietic stem/progenitor cell marker) and CD14 (monocyte/macrophage differentiation marker) in cells was evaluated by FACS analysis, with detection of the CD34 and CD14 antigen by PE-anti-CD34 and FITC-anti-CD14 monoclonal antibodies (BD Biosciences, Oakville, ON). Briefly, the cells were stained in PBS (Ca- and Mg-free) supplemented with 5% BGS. After the final wash, cells were fixed in 2% paraformaldehyde prior to FACS analysis, which was performed by FACscan (Becton-Dickinson, San Jose, Calif.) using PE-goat-anti-mouse immunoglobulin (IgG) as the isotype control. To eliminate any nonspecific binding, the same ratio of fluorochrome/protein for the isotype control and specific antibody was used.

Example 6

Use with Cytokines

The use of ultrasound can achieve synergistic effect when combined with cytokine cocktail (SCF: 100 ug/ml, TPO:50 ug/ml, Flt3-ligand: 50 ug/ml) as shown in FIG. 4. In this figure, we can observe, without cytokine cocktail, ultrasound can stimulate modest cell growth (40-60%). However, by combining with cytokine cocktail, ultrasound can achieve synergistic effects on HSPC proliferation.

Compared with the control, FIG. 4 shows the cell count by using the cytokine cocktail alone ("cytokine+control") or using different intensity ultrasound combined with the cytokine cocktail ("cytokine+ . . . "), where different ultrasound intensities are us_A: 40 mW/cm$^2$, us_B: 70 mW/cm$^2$, us_C: 60 mW/cm$^2$, us D; 50 mW/cm$^2$. Before the experiment at "Day 0", the cell counts are $3 \times 10^5$. Use of the cytokine cocktail alone ("Cytokine+control") without ultrasound, the cell counts are $8.1 \times 10^5$ and thus the cell number increase 2.7 fold compared with that at "Day 0".

However, when ultrasound and the cytokine cocktail are combined, synergistic cell growth can be achieved. Cell number increases to $1.25 \times 10^6$ (us_B: 70 mW/cm$^2$) to $1.63 \times 10^6$ (us_C: 60 mW/cm$^2$), which is 1.52 to 2 times more than just using the cytokine alone and is almost 4.15 to 5.41 times more that the control ("Day 0").

Example 8

Stem Cells Remain Undifferentiated

As shown in FIG. 5, ultrasound treated HSPC (human hematopoietic stem/progenitor cells) do not differentiate. Flowcytometry (FACS) was performed at day 5 to detect CD34 and CD14 in LIPUS-expanded HSPC. At all different intensities (A: 40 mW/cm$^2$, B: 70 mW/cm$^2$, C: 60 mW/cm$^2$, D: 40 mW/cm$^2$) the vast majority of the stem cells remained CD34 positive.

Example 9

In Vivo Function of LIPUS-Expanded HSPC

A) Human Cell Engraftment Assay
8- to 10-week-old 30 NOD/SCID mice are sublethally irradiated (375 cGy, from a 60 Co source) and retro-orbitally given transplants with LIPUS-expanded human hematopoietic stein/progenitor cells (HSPC) or control HSPC as indicated (2×105 cells/mouse; 10 mice: control HSPC, 10 mice: negative control, only PBS, 10 mice: LIPUS-expanded HSPC) 24 hours after irradiation. NOD/LtSz-Prkdcscid (NOD/SCID) mice are bred and maintained under defined flora conditions in individually ventilated (high-efficiency particle arresting filtered air) sterile microisolater cages. As soon as they are irradiated, they are maintained on oral antibiotic (Neomycin 2 mg/ml in autoclaved acidified water, pH 2.0) in order to prevent infections.

Human cell engraftment are assayed 5 weeks after transplantation from bone marrow and peripheral blood by flow cytometry (FACS) using specific antihuman CD45-allophyocyanin (APC), anti-CD19-PE, anti-CD33-PE, anti-CD34-APC, and anti-CD38-PE monoclonal antibodies (mAbs; all obtained from BD PharMingen). Noninjected mice are used as negative controls.

B) Homing Assay
8- to 10-week-old 60 NOD/SCID mice are sublethally irradiated (375 cGy, from a 60 Co source) and retro-orbitally given transplants with LIPUS-expanded human hematopoietic stem/progenitor cells (HSPC) or control HSPC as indicated (2×105 cells/mouse; 10 mice: control HSPC, 10: negative control, only PBS, 10: LIPUS-expanded HSPC) 24 hours after irradiation. Cells are recovered from the murine bone marrow and spleen either 2 or 16 hours after transplantation and analyzed for the presence of human cells using human-specific anti-CD34 and anti-CD38 mAbs acquiring at least 106 cells/sample by FACS.

The following criteria are used to evaluate the quality of the stem cells by using in vivo and in vitro functional assays:

(i) Cell viability or cell counts: The viability of stem cells are determined by trypan blue dye and propidium iodide (PI) exclusion, whereas cell proliferation is monitored by MTT cell proliferation assay.

(ii) Phenotypic characterization: CD 34 is the most common marker used to obtain enriched populations of human hematopoietic stem/progenitor cells (HSPC) for research or clinical use. In fact, CD34+ and CD38− cells are more primitive, pluripotent HSPC. In order to assess the self-renewal and differentiation capacity of LIPUS-manipulated cells, the expression of CD34, CD38 and other hematopoietic markers such as CD14 and CD15 (myelomonocytic/monocytic markers) which are associated with differentiation are assessed by flow cytometry (FACS).

(iii) Colony forming unit assay (CFU) assay: The most common approach used to quantify multi-lineage- or single lineage-committed hematopoietic progenitors, is the evaluation of colony-forming cells (CFCs) or colony-forming units (CFUs). This technique utilizes viscous or semi-solid matrices and culture supplements that promote their proliferation and differentiation and allow the clonal progeny of a single progenitor cell to stay together and thus form a colony of more mature cells. Moreover, the efficiency of re-plating the cells from primary colonies grown in semisolid medium could be used to detect and quantitate the self-renewal in vitro. Therefore, differentiation and self-renewal capacity of ultrasound stimulated-expansion of cord blood (CB) CD34+ cells are assessed by using CFU assay.

(iv) Quantitate Frequency of long-term culture-initiating cells (LTC-IC) and Study their Phenotypic and Functional Properties: Primitive hematopoietic progenitors capable of initiating and sustaining myelopoiesis for several weeks in long-term culture have been called long-term culture-initiating cells (LTC-IC). The frequency of LTC-IC in CB cells are determined using the standard LTC-IC assay.

(v) Stem cell functional assay in vivo: In addition to the functional assays in-vitro to evaluate the stem cell function, in-vivo functional assay is also used for evaluation. The hallmark of HSPC is their ability for stable long-term reconstitution of the entire hematopoietic system after transplantation into myeloablated recipients. Transplantation assays in mice have proven to be excellent experimental models to study the basic principles of stem cell biology, including immunophenotypic characterization, homing ability and engraftment kinetics. Evaluation of the homing and engraftment of human HSCs in an experimental setting has become possible thanks to the development of xenogeneic transplantation models in immunodeficient mouse strains (e.g., NOD/SCID). Thus, the engraftment and homing efficiency of LIPUS-expanded CB CD34+ cells are evaluated by NOD/SCID repopulating assay.

What is claimed is:

1. A method of increasing the rate of growth of an animal stem cell culture, comprising exposing the animal stem cell culture to ultrasound having a frequency from greater than about 1 MHz to about 10 MHz,
wherein the ultrasound is pulsed.

2. The method of claim 1, wherein the frequency of the ultrasound is from greater than about 1 MHz to 2 MHz.

3. The method of claim 2, wherein the frequency of the ultrasound is between about 1.4 MHz and about 1.6 MHz.

4. The method of claim 3 wherein the frequency of the ultrasound is about 1.5 MHz.

5. The method of claim 1, wherein the intensity of the ultrasound is from about 1 mW/cm$^2$ to about 5 W/cm$^2$.

6. The method of claim 5, wherein the intensity of the ultrasound is from about 10 mW/cm$^2$ to about 150 mW/cm$^2$.

7. The method of claim 1, wherein the ultrasound is applied in periodic intervals.

8. The method of claim 7 wherein the ultrasound is applied in one or more intervals totaling less than about 60 minutes in a 24 hour period.

9. The method of claim 8 wherein the ultrasound is applied in a single interval of about 10 to about 20 minutes in a 24 hour period.

10. The method of claim 1, wherein the animal stem cell culture comprises hematopoietic stem cells.

11. The method of claim 10, wherein the hematopoietic stem cells are CD34+ hematopoietic stem/progenitor cells.

12. The method of claim 1, wherein the animal stem cell culture comprises human stem cells.

13. The method of claim 1, wherein the animal stem cell culture comprises adult stem cells.

14. The method of claim 1, wherein the animal stem cell culture comprises mammalian stem cells.

15. The method of claim 1, wherein the animal stem cell culture comprises a cytokine.

16. The method of claim 1, further comprising engrafting cells from the animal stem cell culture.

17. The method of claim 1, wherein:
the frequency of the ultrasound is from greater than about 1 MHz to 2 MHz,
the ultrasound is applied in periodic intervals,
the animal stem cell culture comprises adult human hematopoietic stem cells, and
the animal stem cell culture comprises a cytokine.

18. The method of claim 17, further comprising engrafting cells from the animal stem cell culture.

* * * * *

UNITED STATES PATENT AND TRADEMARK OFFICE
CERTIFICATE OF CORRECTION

| | | |
|---|---|---|
| PATENT NO. | : 9,005,942 B2 | Page 1 of 1 |
| APPLICATION NO. | : 13/060851 | |
| DATED | : April 14, 2015 | |
| INVENTOR(S) | : Jie Chen et al. | |

It is certified that error appears in the above-identified patent and that said Letters Patent is hereby corrected as shown below:

On the Title Page

References Cited Item (56)

Page 2.

Col. 1, Line 29, please delete "A."
Col. 1, Line 30, please delete ""Handbook of Plant-Based Biofuels"," and insert --Handbook of Plant-Based Biofuels,--
Col. 2, Line 9, please delete "Gamauf." and insert --Gamauf,--

Page 3.

Col. 1, Line 57, please delete "332.351" and insert --332-351--
Col. 2, Line 54, please delete "Viol." and insert --Biol.--

Signed and Sealed this
Twenty-fifth Day of August, 2015

Michelle K. Lee
*Director of the United States Patent and Trademark Office*